US00PP21545P2

(12) United States Plant Patent
Ui et al.

(10) Patent No.: US PP21,545 P2
(45) Date of Patent: Nov. 30, 2010

(54) ***PETUNIA-CALIBRACHOA* PLANT NAMED 'SAKPXC005'**

(50) Latin Name: ***Petunia-Calibrachoa* hybrid**
Varietal Denomination: SAKPXC005

(75) Inventors: Akinobu Ui, Iwata (JP); Shin Ishikawa, Kakegawa (JP)

(73) Assignee: Sakata Seed Company, Yokohama (JP)

( * ) Notice: Subject to any disclaimer, the term of this patent is extended or adjusted under 35 U.S.C. 154(b) by 0 days.

(21) Appl. No.: 12/460,939

(22) Filed: Jul. 27, 2009

(51) Int. Cl.
*A01H 5/00* (2006.01)

(52) U.S. Cl. ..... Plt./263.1

(58) Field of Classification Search ..... Plt./263.1
See application file for complete search history.

*Primary Examiner*—Kent L Bell
(74) *Attorney, Agent, or Firm*—Jondle & Associates, P.C.

(57) ABSTRACT

'SAKPXC005' is a new *Petunia-Calibrachoa* hybrid particularly distinguished by having a vanilla and blue-purple flower color and medium to large flower size.

1 Drawing Sheet

Genus and species: *Petunia-Calibrachoa* hybrid.
Variety denomination: 'SAKPXC005'.

BACKGROUND OF THE INVENTION

The present invention comprises a new and distinct cultivar of *Petunia-Calibrachoa* hybrid referred to by the variety name 'SAKPXC005'. Variety 'SAKPXC005' originated from a hybridization in Kakegawa, Japan in October of 2004. The male parent was a proprietary hybrid *Calibrachoa* line named '04-94', which had a bronze with vein flower color, medium-large flower size and a creeping plant habit. The female parent was a proprietary hybrid *Petunia* line named '04F-31 K', which had a pink with eye flower color, medium flower size and a semi-mounding plant habit.

In October 2004, the new *Petunia-Calibrachoa* variety was developed using an intergeneric cross between *Petunia hybrida* and a *Calibrachoa hybrida* species. After crossing the parent lines, 1,500 ovules were removed from flowers on the female parent and cultured by standard ovule culture techniques. In December 2004, one intergeneric hybrid plantlet was transplanted to soilless media for greenhouse culture and acclimatization.

In April 2005, the selected plant was vegetatively propagated by cuttings to produce rooted cuttings. The selected plant was transplanted to an open field and evaluated for flower color and plant growth habit through July 2005. The selected plant, named 'SAKPXC005', has a vanilla and blue-purple with vein flower color, medium-large flower size and a mounding plant habit. From August to November 2005, 'SAKPXC005' was vegetatively propagated and transplanted into a field. In November 2005, 'SAKPXC005' was found to reproduce true to type in successive generations of asexual propagation.

SUMMARY OF THE INVENTION

The following are the most outstanding and distinguishing characteristics of this new cultivar when grown under normal horticultural practices in Kakegawa, Japan.

1. Vanilla and blue-purple flower color;
2. Medium to large flower size; and
3. A mounding plant growth habit.

DESCRIPTION OF PHOTOGRAPHS

This new *Petunia-Calibrachoa* plant is illustrated by the accompanying photographs which show the plant's form, foliage and flowers. The photographs are of a plant five and a half months old grown in Salinas, Calif. in the Spring of 2009. The colors shown are as true as can be reasonably obtained by conventional photographic procedures.

Figure 1:
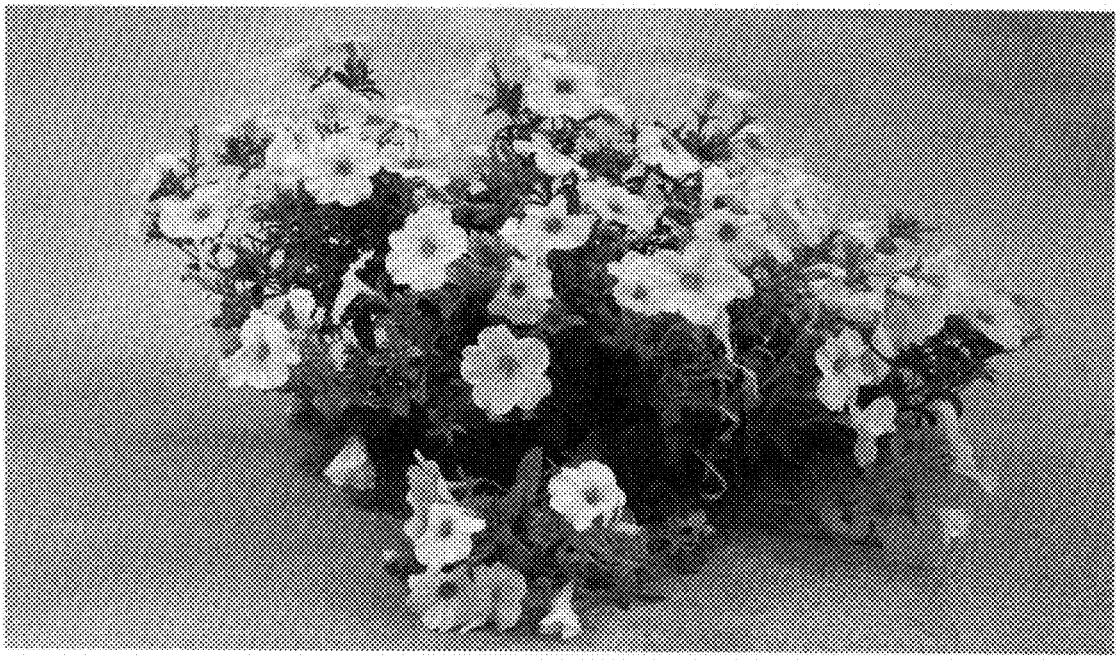

FIG. 1. shows overall plant habit.

Figure 2:
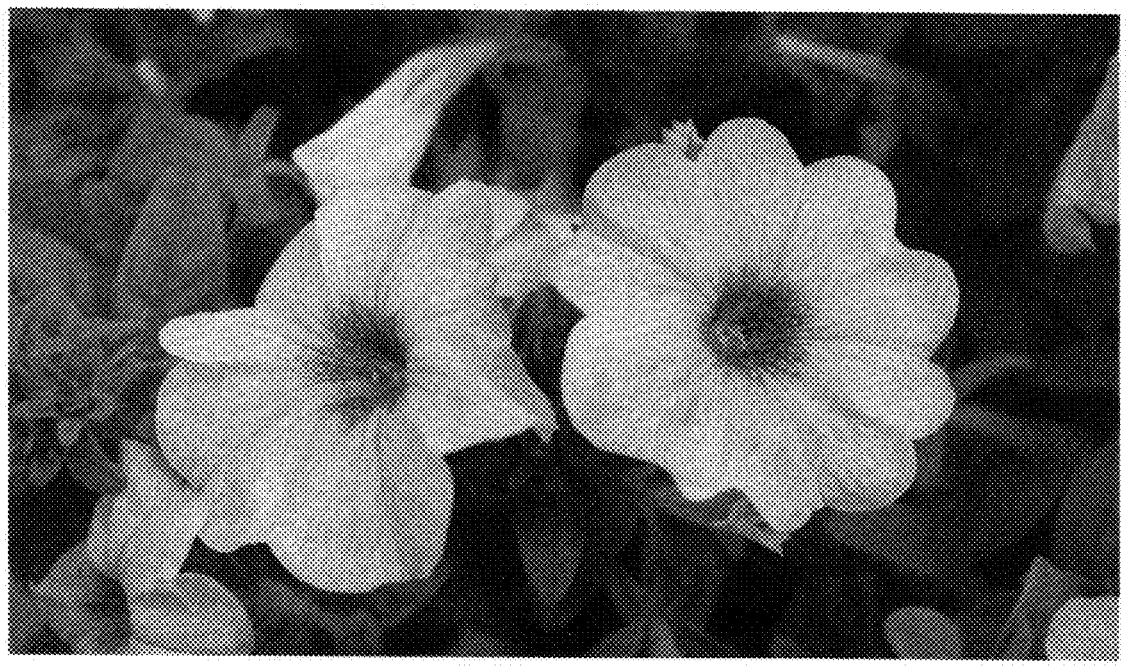

FIG. 2. shows the mature flowers.

DESCRIPTION OF THE NEW CULTIVAR

The following detailed description sets forth the distinctive characteristics of 'SAKPXC005'. The data which define these characteristics were collected from asexual reproductions carried out in Salinas, Calif. The detailed description was taken from plants grown under greenhouse conditions for approximately five and a half months from transplanting of rooted cuttings. Color references are to The R.H.S. Colour Chart of The Royal Horticultural Society of London (R.H.S.), $4^{th}$ Edition.

DETAILED BOTANICAL DESCRIPTION

Classification:

*Family.*—Solanaceae.

*Species.*—*Petunia-Calibrachoa* intergeneric hybrid.

*Common name.*—Petchoa.

Parentage:

*Male.*—Hybrid proprietary *Calibrachoa* plant line '04-94'.

*Female.*—Hybrid proprietary *Petunia* plant line '04F-31K'.

Plant description:

*Life cycle.*—Tender perennial.

*Form.*—Decumbent, branching.

*Habit.*—Mounding, semi-trailing.

*Height* (*from soil line to top of foliage*).—20.0 cm to 22.0 cm.

*Spread.*—65.0 cm to 66.0 cm.

Propagation:

*Type cuttings.*—Vegetative cuttings.

*Time to produce a rooted cutting.*—4 weeks.

*Time to bloom from propagation.*—8 to 10 weeks.

Environmental conditions for plant growth: The terminal 1.0 to 1.5 inches of an actively growing stem was excised. The vegetative cuttings were propagated in four weeks. The base of the cuttings were dipped for 1 to 2 seconds in a 1:9 solution of DIP 'N GROW (1 solution: 9 water) root inducing solution immediately prior to sticking into the cell trays. Cuttings were stuck into plastic cell trays having 98 cells, and containing a moistened peat moss-based growing medium. For the first week, the cuttings were misted with water from overhead for 20 seconds, one time per hour. For the second week, the cuttings were misted one time every 2 hours for 10 seconds. After that time, the cuttings were misted occasionally until sufficient roots were formed. Rooted cuttings were transplanted and grown in 20 cm diameter plastic pots in a glass greenhouse located in Salinas, Calif. Pots contained a peat moss-based growing medium. Soluble fertilizer containing 20% nitrogen, 10% phosphorus and 20% potassium was applied once a day or every other day by overhead irrigation. Pots were top-dressed with a dry, slow release fertilizer containing 20% nitrogen, 10% phosphorus and 18% potassium. The typical average air temperature was 24° C.

Stems:

*Stem color.*—RHS 143B (Green).

*Pubescence.*—Heavy.

*Pubescence color.*—RHS N155A (White).

*Stem description.*—Circular, cross section.

*Stem diameter.*—0.4 cm.

*Stem length.*—3.0 cm from soil line to first node, 25.0 cm total length Internode length: 2.0 cm.

Leaves:

*Arrangement.*—Alternate.

*Shape.*—Elliptical.

*Apex.*—Obtuse.

*Base.*—Attenuate.

*Margin.*—Entire.

*Surface.*—Dull.

*Surface pubescence.*—Moderate.

*Pubescence color.*—RHS N155A (White).

*Venation.*—Pinnate.

*Venation color.*—Upper surface: RHS 143A (Green). Lower surface: RHS 143B (Green).

*Length.*—4.5 cm.

*Width.*—2.2 cm.

*Color.*—Upper surface: RHS 143A (Green). Lower surface: RHS 143B (Green).

*Fragrance.*—Absent.

Flowers:

*Flowering habit.*—Indeterminate.

*Flower type.*—Solitary.

*Flowering requirements.*—Will flower so long as day length is greater than 12 hours and temperature exceeds 13° C.

*Duration of flowers.*—5 days.

*Corolla.*—5 petals, fused.

*Shape.*—The flowers are funnel shaped with five fissures and a shallow, yet slight, indentation of the petal tip at the midvein.

*Fragrance.*—Absent.

Flower buds:

*Surface.*—Pubescent.

*Length.*—3.0 cm.

*Diameter.*—0.5 cm.

*Shape.*—Ovate.

*Color.*—RHS 144C (Yellow-green) with RHS N187A (Greyed-purple) veins.

*Peduncle.*—Length: 3.5 cm. Diameter: 0.15 cm. Color: RHS 143B (Green) with RHS N79A (Purple) toward sepals. Texture: Dull, slight pubescence. Anthocyanin color: Very slight, color is RHS N79A (Purple).

Flower description:

*Flower depth.*—1.5 cm.

*Flower tube length.*—3.0 cm.

*Flower tube diameter.*—1.0 cm.

*Flower diameter.*—5.5 cm.

*Pedicel color*—RHS 143B (Green) with RHS N79A (Purple).

*Calyx.*—5 sepals fused below the middle.

*Sepals.*—Shape: Elliptical. Apex: Obtuse. Margin: Entire. Length: 1.8 cm. Diameter: 0.4 cm. Sepal color: Upper surface: RHS 143A (Green). Lower surface: RHS 143B (Green).

*Petal.*—Shape: The flowers are funnel shaped with five fissures and a shallow, yet prominent, indentation of the petal tip at the midvein. Length: 2.0 cm. Apex: Truncate. Margin: Entire. Base: Fused. Pubescense: Glabrous. Lobe length: 2.0 cm. Lobe width: 2.5 cm. Color: Lobe: Upper surface: RHS N155B (White) with splashes of RHS 75A (Purple) throughout lobes and at edge of lobes. Veins are also RHS 75A (Purple) Lower surface: RHS N155B (White) with RHS 150C (Yellow-green) veins.

*Corolla tube color.*—Inner: RHS 5A (Yellow) with RHS 187A (Greyed-purple) veins. Outer: RHS 155B (White) with RHS 150C (Yellow-green) veins.

*Fragrance.*—Absent.

Reproductive organs:

*Stamen number.*—5, free.

*Stamen color.*—Anther color: RHS 6B (Yellow). Filament color: RHS 2C (Yellow).

*Pollen color.*—RHS 6D (Yellow).

*Ovary.*—Superior.

*Placenta arrangement.*—Central.

*Pistil number.*—1 per inflorescence.

*Pistil length.*—1.9 cm.

*Stigma color.*—RHS 149A (Yellow-green).

*Style length.*—1.7 cm.

*Style color.*—RHS 145C (Yellow-green).

Fruit/seed set: No fruit or seeds produced.

Disease and insect resistance: 'SAKPXC005' has excellent resistance to rain, heat and drought. A temperature below 10° C. is not optimal. Plants are susceptible to *Botrytis*, powdery mildew, various stem and root rots, and certain viruses, like Tobacco Mosaic Virus and Impatiens Necrotic Spotted Virus. Plants can be infested with aphids, leafminer, whitefly and various Lepitopdera.

COMPARISON WITH PARENTAL LINES AND KNOWN CULTIVARS

'SAKPXC005' is a distinct variety of *Petunia-Calibrachoa* due to its vanilla and blue-purple flower color and mounding growth habit. 'SAKPXC005' is distinguished from its parents mainly by flower color and plant growth habit as shown in Table 1 below.

TABLE 1

| Characteristic | 'SAKPXC005' | Male Parent: '04-94' | Female Parent: '04F-31K' |
|---|---|---|---|
| Flower color | Vanilla and blue-purple | Bronze with vein | Pink with eye |
| Plant habit | Mounding | Creeping | Semi-mounding |

'SAKPXC005' is a distinct variety of *Petunia-Calibrachoa* due to its vanilla and blue-purple flower color. 'SAKPXC005' is most similar to the variety 'Kakegawa S91' (U.S. Plant Pat. No. 19,122); however, there are differences in the petal color as described in the table below (color references are to The R.H.S. Colour Chart of The Royal Horticultural Society of London (R.H.S.), 4$^{th}$ Edition):

TABLE 2

| Characteristic | 'SAKPXC005' | 'Kakegawa S91' |
|---|---|---|
| Petal color, upper surface | RHS N155B (White) with splashes of RHS 75A (Purple) throughout lobes and at edge of lobes. Veins are also RHS 75A (Purple) | RHS 29A (Orange) with RHS N77A (Purple) veins |
| Petal color, lower surface | RHS N155B (White) with RHS 150C (Yellow-green) veins | RHS 29C (Orange) with RHS 149C (Yellow-green) veins |

We claim:

1. A new and distinct cultivar of *Petunia-Calibrachoa* hybrid plant as shown and described herein.

* * * * *